United States Patent [19]

Lednicer

[11] 4,346,101
[45] Aug. 24, 1982

[54] BENZAMIDE DERIVATIVE ANALGESICS

[75] Inventor: Daniel Lednicer, Columbus, Ohio

[73] Assignee: The Upjohn Company, Kalamazoo, Mich.

[21] Appl. No.: 213,963

[22] Filed: Dec. 8, 1980

[51] Int. Cl.³ .................. A61K 31/335; A61K 31/165; C07D 319/04; C07C 103/22

[52] U.S. Cl. ..................................... 424/278; 424/324; 549/333; 549/342; 564/161; 564/166; 564/168; 564/177; 564/185

[58] Field of Search ...................... 260/340.9 R, 340.7; 564/161, 166, 168, 177, 185; 424/278, 324

[56] References Cited

U.S. PATENT DOCUMENTS 3,975,443 8/1976 Harper ................................ 260/558
4,065,573 12/1977 Lednicer ............................. 424/278
4,098,904 7/1978 Szmuszkovicz ............. 260/326.4 X
4,212,878 7/1980 Lednicer et al. ............ 260/340.9 R

OTHER PUBLICATIONS

*British Journal of Pharmacology*, 49 (1973), "Anti-Nociceptive Effects in N-Substituted Cyclohexylmethylbenzamides" by R. T. Brittain et al., pp. 158P-159P. *Journal of Medicinal Chemistry*, 17 (1974), "1-(3,4-Dichlorobenzamidomethyl)Cyclohexyldimethylamine and Related Compounds as Potential Analgesics" by N. J. Harper et al.

Primary Examiner—Ethel G. Love
Attorney, Agent, or Firm—John T. Reynolds

[57] ABSTRACT

Benzamide derivative analgesic compounds of the formula

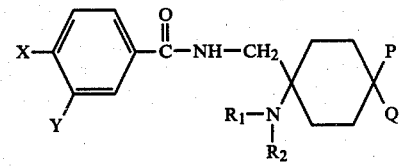

wherein P, Q, $R_1$, $R_2$, X and Y are as defined in the specification, e.g., 3,4-Dichloro-N-[[8-(dimethylamino)-1,4-dioxaspiro[4.5]dec-8-yl]methyl]benzamide, and their pharmacologically acceptable salts, have analgesic drug properties with a low ratio of analgesic to sedative activity for use as analgesic drugs in mammalian animals, including humans.

23 Claims, No Drawings

BENZAMIDE DERIVATIVE ANALGESICS

INTRODUCTION

This invention relates to benzamide derivative compounds useful as analgesic drugs. More particularly, this invention provides a group of new N-[(4-substituted-1-aminocyclohex-1-ylmethyl]benzamide derivative compounds which have been found to have potent analgesic properties and which have a low sedative potential.

BACKGROUND OF THE INVENTION

R. T. Brittain et al., in Brit. J. Pharm., 49, 158(1973) and N. J. Harper et al., in J. Med. Chem., 17, 1188 (1974), disclose some 1-amino-1-benzamidomethylcyclohexane analgesic compounds of the formulae

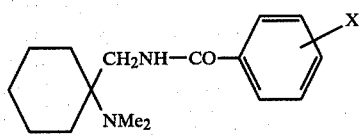

wherein X is hydrogen, 4-F, 3,4-di-Cl,2-Cl, 3-Cl or 4-Cl and Me denotes methyl;

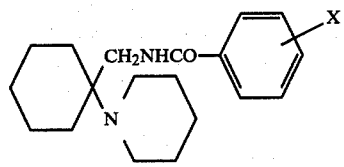

where X is 4-fluoro, 3,4-dichloro or 2-Chloro or 4-Chloro; and

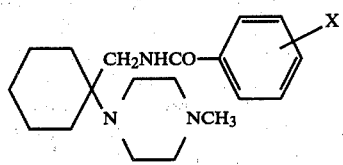

where X is hydrogen or 3,4-dichloro.

Also, Harper et al., in U.S. Pat. No. 3,975,443, in which numerous patent and other publication references are cited, discloses a class of compounds of the formula

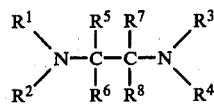

but claims only 1-(3,4-dichlorobenzamidomethyl)-cyclohexyldimethylamine. These compounds are stated to have utility as oral analgesics.

In addition, Lednicer U.S. Pat. No. 4,065,573, issued Dec. 26, 1978, discloses analgesic compounds of the formula

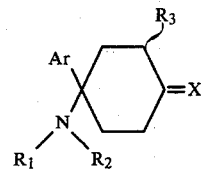

wherein X is oxo or

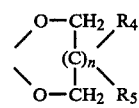

wherein n is zero or 1, $R_1$ is hydrogen or $C_1$ to $C_8$-alkyl, $R_2$ is inter alia hydrogen or $C_1$ to $C_8$-alkyl, $R_4$ is hydrogen or methyl, $R_5$ is hydrogen, phenyl, —$CH_2$-alkenyl wherein alkenyl is of 2 to 4 carbon atoms, inclusive, or methyl; aryl (Ar-) is thiophene or

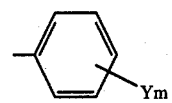

wherein m is zero, one or two, and Y is halogen, $CF_3$, $C_1$ to $C_4$-alkyl, $C_1$ to $C_4$-alkoxy, hydroxy, $C_3$ to $C_6$-cycloalkyloxy, $C_2$ to $C_4$-alkanoyloxy, $C_1$ to $C_4$-alkylthio, or

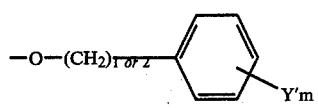

wherein $Y'$ is halogen, —$CF_3$, $C_1$ to $C_4$-alkyl, $C_1$ to $C_4$-alkyloxy, $R_1$ is hydrogen, $C_1$ to $C_8$-alkyl, $R_2$ is hydrogen, $C_1$ to $C_8$-alkyl, —$CH_2$-alkenyl wherein alkenyl is 2 to 8 carbon atoms, acetyl, cycloalkylalkyl having 3 to 6 carbons in the cycloalkyl and 1 to 3 carbons in the alkyl, β-hydroxyethyl, carbethoxymethyl, $C_3$ to $C_6$-cycloalkyl,

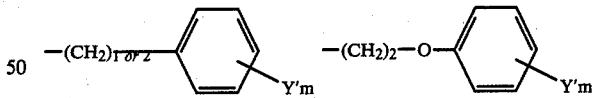

and $R_3$ is hydrogen, $C_1$ to $C_5$-alkyl, and the acid addition salts thereof, among others. However, such compounds do not have geminal 1-amino-1-amidomethyl substituents similar to those described and claimed herein.

Lednicer/Szmuszkovicz U.S. Pat. No. 4,212,878 discloses some N-[1-Amino-4-(mono- or di-oxygen-group-substituted)cyclohex-1-yl)methyl]-phenylacetamide derivatives, e.g., 2-(3,4-dichlorophenyl)-N-[[8-(1-pyrrolidinyl)-1,4-dioxaspiro[4.5]dec-8-yl]methyl]acetamide, and their pharmacologically acceptable salts, which have analgesic properties with lower physical dependence liability than morphine or methadone, for use as analgesic drugs in mammalian animals including humans.

In addition, Szmuszkovicz U.S. Pat. No. 4,098,904 discloses some N-(2-aminocycloaliphatic)benzamides, e.g., N-methyl-N-[2-(N-pyrrolidinyl)cyclohexyl]-3,4-dichlorobenzamide, and their pharmacologically acceptable salts, but such compounds do not have the amino group and the amido group bonded through the same cycloaliphatic ring carbon atom.

Those skilled in the analgesic chemical and pharmacology arts continue to search for new and useful compounds which have good analgesic activity with minimum amounts of sedation side effects.

OBJECTS OF THE INVENTION

It is an object of this invention to provide some new aminocyclohexyl benzamide derivative compounds which have a high order of analgesic potency while being low in central nervous system (CNS) sedative activity and which compounds are useful in pharmaceutical dosage unit form for alleviating pain in animals, especially humans.

Another object of this invention is to provide compositions useful in pharmaceutical dosage unit forms for alleviating pain in animals while reducing or eliminating a sedating side effect that some analgesic compounds have.

Another object of this invention is to provide a method for alleviating pain in valuable animals and humans while reducing or eliminating sedative side effects that some analgesic drugs have.

Other objects, aspect and advantages of this invention will become apparent from the remaining specification and claims which follow.

SUMMARY OF THE INVENTION

Briefly, this invention provides some rather specifically structured 1-Amino-4-substituted cyclohex-1-yl-methyl substituted benzamides, e.g., 3,4-dichloro-N-[[8-(dimethylamino)-1,4-dioxaspiro[4.5]-dec-8-yl]methyl]-benzamide, and the pharmacologically acceptable salts thereof, which compounds have been found to have a unique combination of high analgesic potency combined with a low order of sedative activity. This combination of properties in this small group of compounds should make these compounds useful as analgesic drugs in treating patients for pain where it is not desired to sedate the patient, e.g., where the patient is a valuable animal who must move during transport, or a human who must drive while having his pain relieved.

DETAILED DESCRIPTION OF THE INVENTION

More particularly, this invention provides some new compounds of the formula

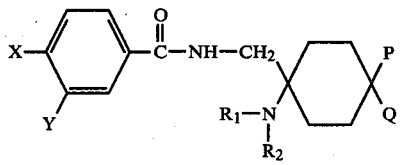

wherein each of $R_1$ and $R_2$ is $C_1$ to $C_3$-alkyl;

P, taken separately, is benzyl or methyl;

Q, taken separately, when P is benzyl or methyl, is hydrogen or hydroxy;

P and Q, taken together, complete an alkylene dioxy ring group selected for the group consisting of ethylene dioxy, 1,3-propylenedioxy and 1,3-propylenedioxy having one or two methyl groups on carbon two of the propylene chain (atom number 3 in the resulting spiro ring);

X is selected from the group consisting of a halogen having an atomic number of from 9 to 35, trifluoromethyl, $C_1$ to $C_3$-alkyloxy, or nitro;

Y is a halogen having an atomic number of from 9 to 35, hydrogen, methoxy, and Y is hydrogen when X is trifluoromethyl or nitro, and X can be methoxy when Y is bromine, and the hydrates and pharmacologically acceptable salts thereof.

In the above formula I compounds, the term "$C_1$ to $C_3$-alkyl" means methyl, ethyl, n-propyl and isopropyl. Methyl and ethyl are preferred as $R_1$ and $R_2$ for reasons of ease of use in preparing the compounds and cost economy in processing. The term "halogen having an atomic number of from 9 to 35" means fluorine, chlorine and bromine.

It will be apparent to those in the chemical art that these compounds are sometimes obtained in isomeric forms, which forms satisfy the above chemical general formula I but which forms may have different melting points, crystalline properties or solvation or hydration properties. However, to date in our studies in compounds of the above type which have different isomeric forms, both isomers of which have been tested, both isomers have shown analgesic potency. This invention includes all such isomeric forms.

A preferred subgroup of the above formula I compounds are those wherein each of $R_1$ and $R_2$ is $C_1$ to $C_3$-alkyl, P and Q are taken together to complete an ethylene dioxy ring, and each of X and Y is a halogen having an atomic number of from 9 to 35, and the pharmacologically acceptable salts thereof. Examples of such compounds include:

3,4-difluoro-N-[[8-(dimethylamino)-1,4-dioxaspiro[4.5]-dec-8-yl]methyl]benzamide 3,4-difluoro-N-[[8-(diethylamino)-1,4-dioxaspiro[4.5]-dec-8-yl]methyl]benzamide 3,4-dibromo-N-[[8-(di-n-propylamino)-1,4-dioxaspiro[4.5]dec-8-yl]methyl]benzamide, and the like, and the pharmacologically acceptable salts thereof.

Another preferred subgroup of formula I compounds are those wherein $R_1$ and $R_2$ are each $C_1$ to $C_3$-alkyl, P and Q are taken together to complete a 1,3-propylenedioxy ring, and each of X and Y is a halogen having an atomic number of from 9 to 35, and the pharmacologically acceptable salts thereof. Examples thereof include:

3,4-dibromo-N-[[9-(diethylamino)-1,5-dioxaspiro[5.5]undec-9-yl]methyl]benzamide, 3,4-difluoro-N-[[9-(di-isopropylamino)-1,5-dioxaspiro[5.5]undec-9-yl]-methyl]benzamide, and 3,4-dichloro-N-[[9-(dimethylamino)-1,5-dioxaspiro[5.5]undec-9-yl]methyl]benzamide, and the like, and the pharmacologically acceptable salts thereof.

Another preferred subgroup of these formula I compounds are those wherein each of $R_1$ and $R_2$ is $C_1$ to $C_3$-alkyl; P is benzyl, Q is hydrogen, and each of X and Y is a halogen having an atomic number of from 9 to 35, and the pharmacologically acceptable salts thereof. Examples include:

N-[[4-benzyl-1-(diethylamino)cyclohexyl]methyl]-3,4-difluorobenzamide,

N-[[4-benzyl-1-(di-n-propylamino)cyclohexyl]methyl]-3,4-dibromobenzamide, and

N-[[4-benzyl-1-(dimethylamino)cyclohexyl]methyl]-3,4-dichlorobenzamide, and the like, and the pharmacologically acceptable salts thereof.

Another preferred subgroup of these formula I compounds are those wherein each of $R_1$ and $R_2$ is $C_1$ to $C_3$-alkyl; P is methyl, Q is hydroxy, and each of X and Y is a halogen having an atomic number of from 9 to 35, and the pharmacologically acceptable salts thereof. Examples include:

3,4-difluoro-N-[[1-(diethylamino)-4-hydroxy-4-methyl-cyclohexyl]methyl]benzamide,
3,4-dibromo-N-[[1-(di-n-propylamino)-4-hydroxy-4-methylcyclohexyl]methyl]benzamide, and the like, and the hydrates and pharmacologically acceptable salts thereof.

Additional useful compounds within formula I include:

α,α,α-trifluoro-N-[[8(diethylamino)-1,4-dioxaspiro[4.5]dec-8-yl]methyl]-p-toluamide.
α,α,α-trifluoro-N-[[9-(di-isopropylamino)-1,4-dioxaspiro[5.5]undec-9-yl]methyl]-p-toluamide,
3-Chloro-N-[[8-(dimethylamino)-1,4-dioxaspiro[4.5]-dec-8-yl]methyl]4-methoxybenzamide,
3-Fluoro-N-[[8-(diethylamino)-1,4-dioxaspiro[4.5]dec-8-yl]methyl]-4-methoxybenzamide,
N-[[8-(diethylamino)-1,4-dioxaspiro[4.5]dec-8-yl]methyl]-4-nitrobenzamide,
N-[[8-(di-n-propyl)-1,4-dioxaspiro[4.5]dec-8-yl]methyl]-4-nitrobenzamide,
3,4-difluoro-N-[[1-(diethylamino)-4-hydroxy-4-methyl-cyclohexyl]methyl]benzamide,
3,4-dibromo-N-[[1-(di-isopropylamino)-4-hydroxy-4-methylcyclohexyl]methyl]benzamide, and the like, and the pharmacologically acceptable salts thereof.

The final compounds of this invention (formula I) can be prepared by methods known in the art, two of which methods are set forth below in detail. In general, except for those compounds wherein P is methyl and Q is hydrogen, the new 1-amidomethyl-1-dialkylaminocyclohexyl compounds of this invention can be prepared by reacting the appropriate diamine of the formula

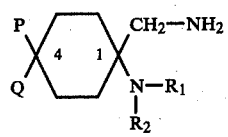

wherein $R_1$, $R_2$, P and Q are as defined above with an aracylimidazole of the formula

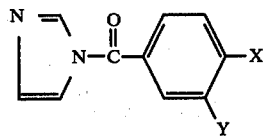

wherein X and Y are as defined above, or with an acyl halide of the formula

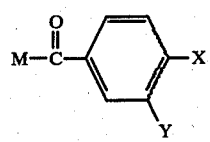

wherein M is chloride or bromide and X and Y are as defined above, in an organic solvent for the reactants, preferably an ether solvent such as diethyl ether, tetrahydrofuran, or the like, until the compound of this invention is produced. An excess of the aracylimidazole or the acyl halide reactant can be used to insure complete reaction of the more expensive diamine, although the aracylimidazole or acyl halide reactants can be mixed in substantially equal proportions to the diamine reactant to effect formation of the desired compound I. This reaction will proceed at an ambient temperature for most combinations of reactants but for some combinations of reactants, variations from the initial to final reaction conditions may vary between about −10° C. and reflux temperature of the mixture, depending upon the reactivity of the reactants, the desired reaction time, the solvent being used, and similar factors of concern to the chemist operating the process. When the reaction has proceeded to substantial completion, the product can be recovered and purified by conventional procedures such as by chromatography, crystallization-recrystallization, and the like.

To prepare a compound wherein P is methyl and Q is hydroxy a 1-amidomethyl-1-(dialkylamino)cyclohexyl ketal compound is deketalized and the resulting amido cyclohexanone is reacted with butyllithium to protect the amido-nitrogen with lithium at low temperature (e.g., dry-ice/acetone bath—about 70° C.) followed by reaction of the lithiated amido-cyclohexanone with a methyl Grignard reagent, e.g., methylmagnesium bromide, in an ether solvent such as THF or diethyl ether or mixtures thereof to form the compound of formula I wherein P is methyl and Q is hydroxy.

Procedures for preparing aracylimidazoles and acyl halide reactants used to form the compounds of this invention are known in the art. See, for example, R. B. Wagner and H. D. Zook, Synthetic Organic Chemistry, 1953, John Wiley & Sons, Chapter 17, page 546, et seq. The aracylimidazole can be prepared in situ by reacting carbonyldiimidazole with the appropriate benzoic acid of the formula

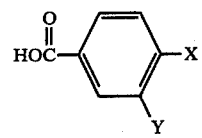

wherein X and Y are as defined above, in an organic solvent. Carbodiimides such as dicyclohexylcarbodiimide can be used in place of the carbonyldiimidazole.

Exemplifying the aracylimidazole method, a solution of about 6.1 mmol of the selected benzoic acid and about 6.1 mmol of 1,1'-carbonyldiimidazole in about 43 ml of tetrahydrofuran (THF) are allowed to stand at room temperature for 3.5 hours. Then a solution of about 6.1 mmol of the selected 4-aminomethyl-4-(dialkylamino)cyclohexanone, or ketal thereof in an inert solvent, e.g., about 13 ml of tetrahydrofuran, is added and the mixture is allowed to stand at room temperature for up to 50 hours with at least occasional stirring or agitation. The solvent is then removed and the residue is dissolved in methylene chloride. The organic fraction, after basic and neutral conventional workup, followed by concentration under vacuum, is dried. The residue is recrystallized yielding the desired benzamide derivative product of this invention.

Using the acid halide method, an ice-cooled solution of about 4.9 mmol of the selected 4-aminomethyl-4-

(dialkylamino)cyclohexanone, or ketal thereof, and about 0.69 ml of triethylamine, or other equivalent trialkylamine, in an inert solvent such as 15 ml of tetrahydrofuran is treated with a solution of 5.0 mmol of the selected benzoyl chloride in 10 ml of tetrahydrofuran. After allowing the mixture to stand with or without agitation for about 18 hours in the cold (−10° to 10° C.—refrigerator overnight), the bulk of the solvent is removed under vacuum and the residue is dissolved in diethyl ether and washed with aqueous sodium bicarbonate solution. The aqueous fraction is extracted once with diethyl ether and the organic fractions are pooled and dried. The residue is recrystallized to yield the desired benzamide derivative product.

The diamine intermediates required for the preparation of compounds of this invention of the formula I, wherein P and Q are taken together to complete an alkylenedioxy ring group, as defined above, or wherein P is benzyl and Q is hydrogen, are prepared by reacting the appropriate 4-P-4-Q-substituted cyclohexanone with potassium cyanide, an acid addition salt of a selected amine of the formula, $HN(R_1)R_2$, in a suitable solvent such as methanol-water in the presence of excess amine of the formula, $HN(R_1)R_2$, to form the respective 4-P-4-Q-1-cyano-1-(dialkylamino)cyclohexane intermediate of the formula II.

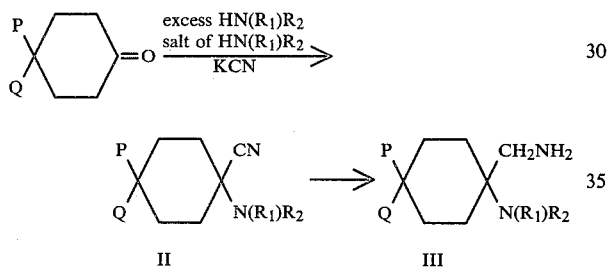

4-Benzylcyclohexanone is prepared as follows. Cyclohexane-1,4-dione, ethylene monoketal is reacted with benzylidenetriphenylphosphorane to afford 4-benzylidenecyclohexanone, ethylene ketal, which is catalytically hydrogenated, e.g., using palladium on carbon, to give 4-benzylcyclohexanone, ethylene ketal. Deketalization with mineral acid, e.g., hydrochloric acid in acetone solution, provides 4-benzylcyclohexanone.

Compounds of formula I are conveniently prepared when 4-cyano-4-aminocyclohexanone ketal (II) is subjected to a lithium aluminum hydride (LAH) reduction in non-alcoholic, non-aqueous inert solvent such as diethyl ether at temperatures which may vary from about −78° C. to about 0° C. It is recommended that an ether solvent such as diethyl ether as opposed to a solvent such as tetrahydrofuran, at relatively low temperatures (below 0° C.), be used to avoid displacement of the cyano group in the preparation. When the reduction is complete, a basic work up of the reaction mixture with sodium hydroxide and water, which results in precipitation of the aluminum salts followed by taking the resultant filtrate to dryness gives the crude 4-P-4-Q-1-aminomethyl-(dialkylamino)cyclohexane intermediates of formula III above. These intermediates (III) can be further purified before reaction with the selected benzoic acid and carbonyl diimidazole or benzoyl chloride, but such purification is not necessary.

If the desired dialkylamine is not readily available, the intermediate diamine of formula VI wherein $R_1$ is $C_1$ to $C_3$-alkyl can be prepared by an alternate route shown below:

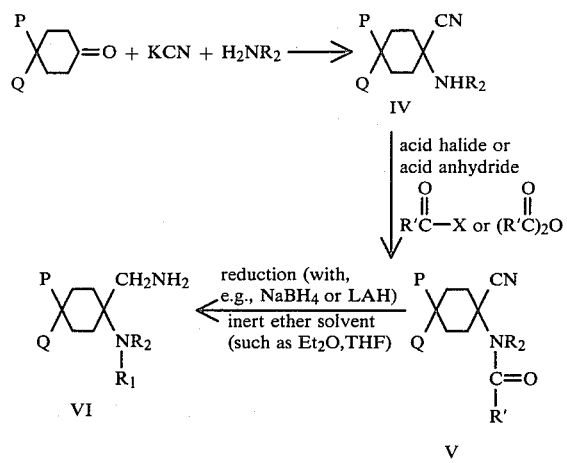

wherein P and Q, taken together, represent an alkylenedioxy group as defined above, $R_2$ is $C_1$ to $C_3$-alkyl, R' is $R_3$-alkyl residue minus one carbon atom, so that R' is H or $C_1$ to $C_2$-alkyl giving $R_3 = 1$ to 3 carbon atoms.

Compounds of this invention of the formula I wherein P is methyl and Q is hydroxy are prepared as follows. A ketal compound of the

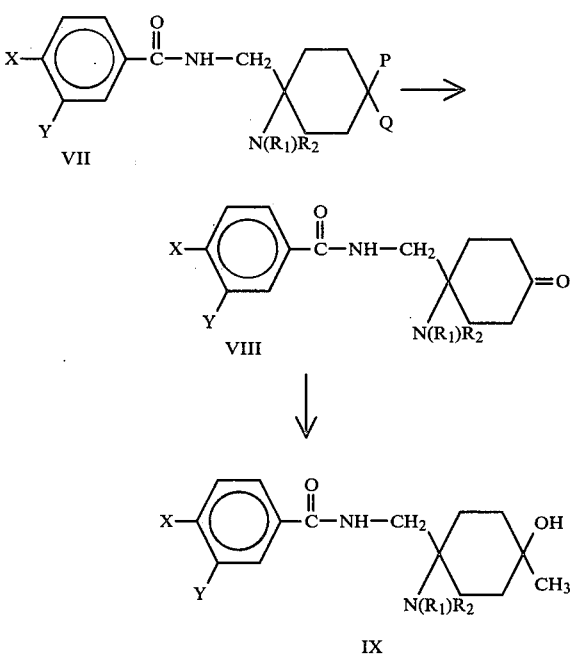

formula VII is deketalized by reacting it with a mineral acid such as hydrochloric acid in aqueous methanol at from about 20° C. to the reflux temperature of the mixture for a time sufficient to produce a ketone of the formula VIII. A ketone of the formula VIII in a suitable solvent such as THF is reacted with butyllithium at a temperature from about 0° C. to −78° C., lower temperatures being preferred, and the resulting lithiated compound is reacted with an ether solution of methylmagnesium bromide to provide after workup a compound of the formula IX.

The reaction of secondary amine and potassium cyanide with the cyclohexanedione mono-ethylene ketal is preferred when the dialkylamine is available or can be readily prepared.

The invention is further described and exemplified by the following detailed examples illustrating how to prepare and use the compounds of the invention but these examples are not intended as defining the limits of the invention.

EXAMPLE 1

3,4-Dichloro-N-[(8-(dimethylamino)-1,4-dioxaspiro[4.5]dec-8-yl)methyl]benzamide

A. Preparation of 8-(dimethylamino)-1,4-dioxaspiro[4.5]decane-8-methanamine

A 0.4 g portion of lithium aluminum hydride (LAH) is cooled in 10 ml of diethyl ether under nitrogen atmosphere. Then 2.0 g of 8-cyano-[1,4-dioxaspiro[4.5]dec-8-yl]dimethylamine (U.S. Pat. No. 4,065,573, Example 41, part B) was added over 20 minutes while stirring at room temperature. Then, in turn, there was added 0.4 ml of water, 0.4 ml of 15 percent sodium hydroxide and 1.2 ml of water. The inorganic gel in the mixture was filtered off. The filtrate was dried by evaporation under vacuum. A thin layer chromatography (tlc) sample analysis showed the residue to be largely one spot material. The Nuclear Magnetic Resonance spectrum (NMR) for this material was very good for the above-named chemical intermediate.

B. Preparation of above-named product

The diamine from Part A, above, (about 0.0095 mol) and 0.96 g. of triethylamine were dissolved in tetrahydrofuran (THF) and cooled over ice. To this solution 2.0 g of 3,4-dichlorobenzoyl chloride was added while stirring. When addition was completed the mixture was allowed to stand in the cold overnight. The bulk of the solvent was removed in a vacuum. Ice was added to the residual reaction mixture and then the resulting mixture was extracted with methylene chloride. The mixture was washed with sodium bicarbonate solution and then dried. The residue weighed 2.8 g. This residue was placed on 300 ml of silica gel and this silica gel column was eluted with 4 percent methanol in methylene chloride. Fractions 25 to 92 gave 2.06 g of the named benzamide product, for which the infrared spectrum (IR) was good. The melting point of this material was 88°–94° C. This material was recrystallized from diethyl ether to obtain 1.5 g of the named benzamide product having a melting point of 92°–96° C. The elemental analysis was as follows:

Anal. Calcd. for $C_{18}H_{24}Cl_2N_2O_3$: C, 55.82%; H, 6.25%; N, 7.23%. Found: C, 55.36%; H, 6.27%; N, 7.00%.

EXAMPLE 2

3,4-Dichloro-N-[[9-(dimethylamino)-3,3-dimethyl-1,5-dioxaspiro[5.5]undec-9-yl]methyl]benzamide, and its p-toluenesulfonate salt

A. Preparation of the 4-aminomethyl-4-(dimethylamino)cyclohexanone 2,2-dimethylpropylene ketal 4-Cyano-4-(dimethylamino)cyclohexanone, 2,2-dimethyl-1,3-propylene ketal is prepared according to Example 50, part B of U.S. Pat. No. 4,065,573.

A 4.07 g (0.016 portion) of this 4-cyano-4-(dimethylamino)cyclohexanone, 2,2-dimethylpropylene ketal in 80 ml of diethyl ether was added to 1.25 g of lithium aluminum hydride (LAH) in 20 ml of diethyl ether cooled in an ice bath and maintained under a nitrogen atmosphere. The resulting reaction mixture was stirred in the cold for four hours. Then, in turn, 1.25 ml of water, 1.25 ml of 15 percent sodium hydroxide solution and 3.75 ml of water were added. The resulting mixture was filtered to separate the inorganic gel, and the filtrate was dried to a crude residue of the named diamine ketal intermediate, 3.90 g having a melting point of 66°–68° C. This material was recrystallized from Skellysolve ® B to a solid weighing 3.38 g, m.p. 65°–67° C. The analysis was:

Anal. Calcd. for $C_{14}H_{28}N_2O_2$: C, 65.58%; H, 11.01%; N, 10.93%. Found: C, 65.80%; H, 10.95%; N, 10.94%.

B. Preparation of the named benzamide

To an ice-cooled solution of 3.38 g (0.013 mol) of the diamine compound from part A and 1.34 g of triethylamine in 40 ml of THF, there was added a solution of the 3,4-dichlorobenzoyl chloride in 30 ml of THF. After stirring to ensure complete reaction, the mixture was allowed to stand in the cold for 17 hours and then the bulk of the solvent was removed in a vacuum. The residue was taken up with methylene chloride and sodium bicarbonate solution. The organic liquid layer was separated and dried to leave as residue 5.2 g of crude product. The crude product was placed over 500 ml of silica gel and eluted first with a mixture of 4 liters of 1.75% methanol in methylene chloride, collecting 200 ml fractions, followed by a mixture of 2.5% methanol in methylene chloride. Fractions 8 to 24 yielded 3.93 g of product, which was taken up in diethyl ether and treated with a solution of 2.2 g of p-toluenesulfonic acid in water to form the p-toluenesulfonate salt of the titled benzamide, 6.79 g, m.p. 205°–208° C. This benzamide salt was recrystallized from a mixture of methylene chloride and ethyl acetate, 5.47 g, m.p. 206°–208° C.

Anal. Calcd. for $C_{28}H_{38}Cl_2N_2O_6S$: C, 55.89; H, 6.37; N, 4.66. Found: C, 55.65; H, 6.21; N, 4.59. C, 55.72; H, 6.63; N, 4.66.

EXAMPLE 3

3,4-Dichloro-N-[[9-(dimethylamino)-1,5-dioxaspiro[5.5]undec-9-yl]methyl]benzamide A solution of 1.13 g (0.0049 mole) of 4-aminomethyl-4-dimethylamino) cyclohexanone, 1,3-propylene ketal and 0.50 g (0.69 ml) of triethylamine in 15 ml of THF was cooled in an ice bath. To this cooled solution there was added a solution of 1.04 g (0.00497 mole) of 3,4-dichlorobenzoyl chloride in 10 ml of THF over 10 minutes while stirring. The reaction mixture was placed in a refrigerator over a weekend. The bulk of the solvent was removed on a rotary evaporator. The residue was taken up in diethyl ether and sodium bicarbonate aqueous solution. The aqueous liquid layer was separated and extracted with diethyl ether. All of the diethyl ether fractions were combined and evaporated to dryness to yield 1.91 g of crude crystalline product, m.p. 109°–122° C. This material was recrystallized from a mixture of methylene chloride and Skellysolve ® B to yield 1.34 g of product, m.p. 131°–135° C. Recrystallization again from methylene Skellysolve ® B gave 1.17 g of named product, m.p. 134.5°–136.5° C. The elemental analysis was as follows:

Anal. Calcd. for $C_{19}H_{26}Cl_2N_2O_3$: C, 56.86; H, 6.53; N, 6.98%. Found: C, 56.87; H, 6.63; N, 6.93%.

EXAMPLE 4

α,α,α-trifluoro-N-[[8-(dimethylamino)-1,4-dioxaspiro[4.5]dec-8-yl]methyl]-p-toluamide A solution of 1.0 g (0.00465 mole) of the ketal from Example 1, part A and 0.47 g (0.65 ml) of triethylamine in 15 ml of THF was cooled in an ice bath. To this cooled solution there was added a solution of 0.97 g (0.00465 mole) of p-trifluoromethylbenzoyl chloride in 10 ml of THF over 10 minutes while stirring. The mixture was placed in a refrigerator overnight. Upon removal from the refrigerator, the bulk of the solvent was removed on a rotary evaporator. The residue was taken up in diethyl ether and aqueous sodium bicarbonate solution. The separated aqueous layer was extracted with diethyl ether. The diethyl ether liquid fractions were pooled and dried to yield the crude, named product, 2.07 g, m.p. 128°–130° C. Recrystallization from a mixture of methylene chloride and Skellysolve ® B gave product weighing 1.56 g, m.p. 129°–130.5° C. The elemental analysis was as follows:

Analysis Calcd. for $C_{19}H_{25}F_3N_2O_3$: C, 59.05; H, 6.52; N, 7.25. Found: C, 59.09; H, 6.59; N, 7.31.

EXAMPLE 5

3-Bromo-N-[[8-(dimethylamino)-1,4-dioxaspiro[4.5]-dec-8-yl]-methyl]-4-methoxybenzamide To a solution of 1.0 g (0.0043 mole) 3-bromo-4-methoxybenzoic acid in 30 ml of THF there was added 0.70 g of 1,1'-carbonyldimidazole. This mixture was stirred at room temperature for 3.5 hours. Then a solution (0.93 g) of the ketal from Example I, part A, in 10 ml of THF was added over five minutes while stirring, and then the mixture was allowed to stand at room temperature. Two days later the bulk of the solvent was removed on rotary evaporator. The residue was partially dissolved in diethyl ether and the solution was washed once with sodium bicarbonate aqueous solution, twice with water, and once with brine solution. The aqueous washes were combined and back washed with diethyl ether. The diethyl ether fractions were pooled and dried to a gummy residue weighing 1.89 g. This residue crystallized upon standing, giving a melting point of 117°–142° C. This crude crystalline material was recrystallized from a mixture of Skellysolve ® B and methylene chloride to give 1.3 g of the titled product, m.p. 143.5°–146° C. Recrystallization again from methylene chloride:Skellysolve ® B gave the named benzamide, weighing 1.20 g, m.p. 143.5–146. It analyzed as follows:

Analysis Calcd. for: $C_{19}H_{27}BrN_2O_4$: C, 53.40%; H, 6.37%; N, 6.56%. Found: C, 53.47%; H, 6.35%; N, 6.46%.

EXAMPLE 6

N-[[8-(Dimethylamino)-1,4-dioxaspiro[4.5]dec-8-yl]methyl]-4-nitrobenzamide

To a solution of 0.39 g (0.0023 mole) of 4-nitrobenzoic acid in 16 ml of THF there was added 0.38 g (0.0023 mole) of 1,1'-carbonyldiimidazole. The mixture was stirred at room temperature for five hours to ensure solution and then treated with a solution of 0.50 g of the ketal from Example I, part A, in 5 ml of THF. The mixture was allowed to stir at room temperature for a time to ensure complete reaction. The bulk of the solvent was removed on the rotary evaporator. The residue was taken up in methylene chloride. This organic liquid solution was washed with sodium bicarbonate aqueous solution, twice with water and once with brine solution to remove water soluble impurities. The aqueous wash solutions were backwashed with diethyl ether. The washed methylene chloride solution of product and diethyl ether washes were combined and concentrated to yield a crystalline solid weighing 0.80 g, m.p. 123°–131° C. Recrystallization from a mixture of methylene chloride:Skellysolve ® B mixture gave 0.76 g of product, m.p. 129°–133° C. Recrystallization again gave named product weighing 0.60 g, m.p. 134°–135° C., which analyzed as follows:

Analysis Calcd. for $C_{18}H_{25}N_3O_5$: C, 59.49; H, 6.93; N, 11.56%. Found: C, 59.51; H, 6.96; N, 11.33%.

EXAMPLE 7

N-[[4-benzyl-1-(dimethylamino)cyclohexyl]methyl]-3,4-dichlorobenzamide

A. Preparation of (1-Aminomethyl-4-benzyl-1-cyclohexyl)dimethylamine

To a mechanically stirred suspension of 15.24 g (0.035 mole) of benzyltriphenylphosphonium bromide in 150 ml of THF there was added first 22 ml of 1.61 N n-butyllithium in pentane and then 5.0 g (0.032 mole) of cyclohexane-1,4-dione, ethylene monoketal in 50 ml of THF. Following 5 hours' heating at reflux the mixture was allowed to cool and was then washed in turn with water and brine. The organic layer was concentrated, and the residue was chromatographed on 1 liter of silica gel, eluting with 20% ethyl acetate in Skellysolve ® B, to afford 7.15 g (97%) of 4-benzylidenecyclohexanone, ethylene ketal as an oil, the nmr spectrum of which is in consonance with the structure.

A mixture of 7.15 g (0.031 mole) of 4-benzylidenecyclohexanone, ethylene ketal and 0.35 g of 10% palladium on carbon in 150 ml of ethyl acetate was shaken under hydrogen until the theoretical gas uptake had been observed (1 hour). The catalyst was then removed on a filter and the filtrate was concentrated in vacuo to give 4-benzylcyclohexanone, ethylene ketal as an oil, the nmr spectrum of which agreed with the structure.

A solution of this oily 4-benzylcyclohexanone, ethylene ketal and 15 ml of 2.5 N HCl in 150 ml of acetone was allowed to stand at 20° to 25° C. overnight. The bulk of the solvent was removed in vacuo, and the precipitated oil was extracted with diethyl ether. The organic layer was washed with water, sodium bicarbonate solution and brine and then concentrated in vacuo. The residue was chromatographed on 600 ml silica gel eluting with 4 L. of 4% acetone in Skellysolve ® B, then 5% acetone in Skellysolve ® B. The crystalline fractions were combined to give 4.65 g (80%) of 4-benzylcyclohexanone, m.p. 40°–44° C. The analytical sample had m.p. 41°–43° C.

Anal. Calcd. for $C_{13}H_{16}O$: C, 82.93; H. 8.57. Found: C, 82.54; H, 8.42. Mass spectrum: parent molecular iron, calcd. 188; Found: m/e 188.

A mixture of 4-benzylcyclohexanone (4.40 g, 0.023 mole), 3.67 g of potassium cyanide, 5.50 g of dimethylamine hydrochloride and 3 ml of methanol in 30 ml of saturated aqueous dimethylamine was stirred at room temperature for 3 days. The mixture was then extracted thoroughly with $CH_2Cl_2$, and the organic layer was concentrated in vacuo. The residue was dissolved in diethyl ether, and the basic material was precipitated with 2 N HCl in diethyl ether. This solid was recrystallized from methylene chloride:ethyl acetate to give 3.91 g (61%) of 4-benzyl-1-cyano-1-(dimethylamino)cyclohexane hydrochloride, m.p. 150°-154° C.

Anal. Calcd. for $C_{16}H_{22}N_2 \cdot HCl$: C, 68.92; H, 8.31; N, 10.05. Found: C, 68.42; H, 8.41; N, 10.30.

A solution of 9.5 mmole of 4-benzyl-1-cyano-1-(dimethylamino)cyclohexane in 25 ml of diethyl ether was added to a suspension of 0.40 g of LAH in 10 ml of diethyl ether cooled in an ice-methanol bath. Following 4 hours' stirring at 20° to 25° C., the mixture was treated in turn with 0.4 ml of water, 0.4 ml of 15% sodium hydroxide and 1.2 ml of water. The inorganic gel was collected on a filter, and the filtrate was concentrated in vacuo to give (1-aminomethyl-4-benzyl-1-cyclohexyl)-dimethylamine was a viscous gum.

B. Preparation of the tilted benzamide

A flask containing 2.82 g (0.11 mode) of (1-aminomethyl-4-benzyl-1-cyclohexyl)dimethylamine and 1.16 g (1.60 ml) of triethylamine in 25 ml of THF was cooled in ice and a solution of 3,4-dichlorobenzoyl chloride (2.40 g) in 15 ml of THF was added. This resulting mixture was allowed to stir and then stand in the cold (refrigerator). Later the bulk of the solvent was removed in vacuo, the residue was taken up in water and diethyl ether. After washing, as above, separation of organic from aqueous phases and concentration, the organic residue (4.51 g) was placed on 400 ml of silica gel. This loaded silica gel was eluted with 10 percent methanol in methylene chloride (40 ml fractions), and there was obtained from fractions 10 to 32 3.30 g of purified product. This named benzamide product was converted to its hydrochloride salt, which salt was recrystallized from a methylene chloride:ethylacetate mixture, giving 2.55 g of the named benzamide hydrochloride salt, m.p. 207°-209° C. Recrystallization again from the same solvents gave 2.28 g, having a m.p. of 207°-209° C. This benzamide salt analyzed as follows:

Analysis Calcd. for $C_{23}H_{29}Cl_3N_2O$: C, 60.60; H, 6.41; N, 6.18. Found: C, 60.17; H, 6.48; N, 6.06.

EXAMPLE 8

3,4-Dichloro-N-[[1-(dimethylamino)-4-hydroxy-4-methylcyclohexyl]methyl]benzamide (isomer B) as its dihydrate, and
3,4-dichloro-N-[[1-(dimethylamino)-4-hydroxy-4-methylcyclohexyl]methyl]benzamide (isomer A)

A. Preparation of
3,4-dichloro-N-[[1-(dimethylamino)-4-oxocyclohexyl]-methyl]benzamide Method 1. The ketal compound prepared as described in Example 1, part B (2.0 g., 5.2 mmoles) and 10 ml of 2.5 N HCl in 20 ml of methanol was heated at reflux overnight. The mixture was allowed to cool, adjusted to pH 8 with solid sodium bicarbonate and the bulk of the solvent was removed in vacuo. The residue was partitioned between water and diethyl ether and the organic layer was concentrated in vacuo. The solid residue was recrystallized several times from acetone:- Skellysolve ® B to afford 0.54 g (30%) of the subtitled ketone, m.p. 142°-144° C.; infrared spectrum: 3300, 1710, 1640 cm$^{-1}$.

Anal. Calcd. for $C_{16}H_{20}Cl_2N_2O_2$: C, 55.98; H, 5.87; N, 8.16. Found: C, 55.79; H. 5.92; N, 8.31.

Method 2. The ketal of p-toluenesulfonate salt prepared as described in Example 2, part B (2.84 g, 5.0 mmoles) and 28 ml of 2.5 N HCl in 28 ml of methanol was allowed to stand at 20° to 25° C. for two hours. The mixture was then made strongly basic with 50% aqueous sodium hydroxide and extracted thoroughly with methylene chloride. The combined extracts were concentrated in vacuo, and the residue was chromatographed over 200 ml of silica gel, eluting with 30% acetone in methylene chloride. The crystalline fractions were combined and recrystallized from acetone:Skellysolve ® B to give 1.23 g (72%) of the subtitled ketone, m.p. 142°-143.5° C.

B. Preparation of the titled benzamides

To a solution of the ketone from part A in 40 ml of THF under nitrogen in a dry ice:acetone bath, there was added 3 ml of 1.68 N butyllithium in pentane. After stirring the mixture 10 minutes in the cold, 3.8 ml (11 mmole) of 2.9 M methylmagnesium bromide in diethyl ether was added. The resulting mixture was stirred at room temperature for 3 days and then treated with 15 ml of saturated ammonium chloride. The organic layer was separated, washed with water and brine and taken to dryness. The residue was chromatographed on a 1×48" column of thin layer chromatography (tlc) grade silica gel and eluted with 7.5 percent methanol in chloroform mixture. There were obtained a series of mixtures followed by the crystalline more polar titled isomer B. This isomer B was recrystallized from chloroform:ethylacetate mixture to give 0.12 g of the above named isomer B, m.p. 215°-216° C., as a dihydrate.

Analysis Calcd. for $C_{17}H_{24}Cl_2N_2O_2 \cdot 2H_2O$: C, 51.69; H, 7.13; N, 7.03. Found: C, 51.62; H, 6.45; N, 6.81.

The less polar fractions were then rechromatographed just as above and then on a prep tlc silica gel plate. The crystalline titled isomer A compound was recrystallized from an ethyl acetate:cyclohexane mixture to give 0.16 g of the above named isomer A, m.p. 154°-157° C.

Analysis Calcd. for $C_{17}H_{24}Cl_2N_2O_2$: C, 56.83; H, 6.73; N, 7.80. Found: C, 57.04; H, 6.80; N, 7.75.

EXAMPLE 9

3,4-Dichloro-N-[[4-benzyl-1-(dimethylamino)-4-hydroxy cyclohexyl]methyl]benzamide, and its p-toluenesulfonate salt (tosylate) and a hydrate thereof To a solution of 2.0 g (5.8 mmole) of 3,4-dichloro-N-[[1-dimethylamino)-4-oxocyclohexyl]methyl]benzamide (Example 8, part A) in 30 ml of THF cooled in a dry ice/acetone there was added an equivalent (3.65 ml) of 1.6 N butyllithium. This mixture was stirred for 10 minutes and allowed to warm to room temperature. There was then added the Grignard reagent obtained from 4.35 g of α-chlorotoluene and 10 g of metallic magnesium in 75 ml of THF. The resulting mixture was allowed to stand for 18 hours at room temperature and then cooled in ice and treated with 50 ml of saturated ammonium chloride. The organic layer was washed with water and brine and taken to dryness. The residue was chromatographed successively on silica gel (3% Methanol:methylene chloride), a 1×48" column plate. The product thus obtained was recrystallized as its tosylate salt to give 0.24 (67% yield) of the titled product, as its monohydrate, m.p. 190°-192° C. The mass spectrum of the product showed the fragments for the major portions of the molecules.

Anal. Calcd. for $C_{30}H_{36}Cl_2N_2O_5S \cdot H_2O$: C, 57.59; H, 6.12; N, 4.47. Found: C, 57.47; H, 6.48; N, 4.72.

This invention also relates to compositions containing a formula I compound as an active ingredient in a pharmaceutical carrier. The compositions are useful in pharmaceutical dosage unit forms of the formula I compounds for systemic administration (oral, rectal and parenteral administration form) in therapy for treating and alleviating pain in humans and valuable animals, including dogs, cats and other commercially valuable and domestic animals.

The term "dosage unit form" as used in this specification and in the claims refers to physically discrete units suitable as unitary dosages for mammalian subjects, each unit containing a predetermined quantity of the essential active ingredient compound of this invention calculated to produce the desired effect, in combination with the required pharmaceutical means which adapt the said ingredient for systemic administration. The specification for the novel dosage unit forms of the invention are dictated by and directly dependent on the physical characteristics of the essential active ingredient and the particular effect to be achieved in view of the limitations inherent in the art of compounding such an essential active material for beneficial effects in humans and animals. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these aminoamide active ingredients in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 to about 250 mg of the essential active ingredient per dosage unit form, divided if desired in dosages of from 1 to 4 times per day, not to exceed about 250 mg per day; the preferred dosage is 1–150 mg per day, which, as aforesaid, may be in the form of a semi-solid, oral, or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain analgesic effects within the aforesaid effective non-toxic range. Expressed otherwise, when used systemically, an amount of the essential active ingredient is provided to a receipient within a range from about 0.01 mg per kg to about 4 mg per kg of body weight of the recipient depending upon the age, weight, condition of the patient or other factors of concern to the physician. Preferred dosages for most applications are about 0.03 to 1.5 mg per kg of body weight.

The useful pharmaceutical dosage unit forms of these compounds in pharmaceutical formulations is preferably adapted for systemic administration to obtain analgesic effects comprising an effective, non-toxic amount of a compound according to formula I or as its pharmacologically acceptable salt.

Further, the invention relates to methods of obtaining analgesic effects in mammals, for example, humans and valuable warm-blooded animals such as dogs, cats, horses and other commercially valuable animals, by administering systemically to the mammals the aforesaid pharmaceutical dosage unit forms supplying an effective, non-toxic amount for analgesic effects. These compounds have an advantage, to a greater or lesser extent, depending upon the particular compound, of having potent analgesic activity (lower $ED_{50}$ numbers), as shown in standard laboratory animal analgesic tests while having substantially low sedative potency (higher $ED_{50}$ numbers in sedation tests) in similar laboratory animal tests. These ratios of high sedative $ED_{50}$ number to analgesic (Flick test) $ED_{50}$ numbers for the claimed compounds herein are shown best by data from tests using subcutenous routes of administration in the standard laboratory animals, indicating that by parenteral administration routes the respective new compounds will have the desired analgesic effect with reduced or minimum sedative side effects. Some of these compounds, such as those of Examples 3, 7 and 8 (isomer B) also show these high sedative/analgesic ratios when given by the oral route of administration, thus suggesting that compounds of those particular types could be administered orally to accomplish similar drug use effects (analgesia without sedative side effects) and without the need for intramuscular or intraveneous administration methods.

The representative detailed Examples 1 to 9 herein of compounds of this invention (formula I) have analgesic screen $ED_{50}$ values, in mg of test compound per kg of animal body weight, by the subcutaneous route, (flick test, pinch test, writhing test) ranging from about 0.03 mg/kg to about 1 mg/kg (indicating very potent analgesic activity) whereas the sedative $ED_{50}$ test data numbers for the same compounds consistently are substantially higher than the corresponding analgesic $ED_{50}$ value numbers, so that the resulting ratios of sedative $ED_{50}$ value to analgesic $ED_{50}$ value, by the same route of administration, are generally higher than about 32, and in the preferred compounds, this sedative/analgesia ratio is substantially higher than 32. By the oral administration routes, some of these compounds are indicated in these tests to be of low potency or inactive (Examples 2, 8, isomer A) while having a high sedative/analgesic activity ratio by the subcutaneous route of administration. At least some of the compounds of the detailed examples (Examples 1, 3, 7 and 8 (isomer B) are shown to have high (greater than 50) sedative/analgesic $ED_{50}$ value ratios by the oral route of administration.

The high sedative/analgesia $ED_{50}$ value ratios for these claimed compounds is believed to be surprising because other similar benzamide compounds having amido-nitrogen methylation did not have such favorable ratios.

The compound of Example 7, N-[[4-benzyl-1-(dimethylamino)cyclohexyl]methyl]-3,4-di-chlorobenzamide, is somewhat unique in that from the analgesic test data available to date it is more active orally than subcutaneously which property should make it more attractive as a possible clinical candidate analgesic compound.

Although not necessary in the embodiments of the inventive concept, additional active ingredients can be incorporated in the present pharmaceutical dosage unit forms as desired. For example, each pharmaceutical dosage unit form may contain therein an amount within the following non-toxic effective ranges: tranquilizers, anti-psychotic and anti-anxiety agents, such as chlorpromazine (5 to 50 mg), thioridazine (5 to 200 mg), haloperidol (0.5 to 5 mg), meprobamate (100 to 400 mg), chlordiazepoxide (5 to 50 mg), diazepam (2 to 15 mg), alprazolam (0.5 to 3 mg), triazolam (0.25 to 1 mg), ketazolam (5 to 300 mg), and ectylurea (100 to 300 mg), barbiturates such as phenobarbital (8 to 60 mg), butabarbital (8 to 60 mg), and amobarbital (16 to 120 mg), analgesics, anti-pyretics and anti-inflammatories, such as aspirin (150 to 600 mg), flurbiprofen (20 to 200 mg), ibuprofen (2 to 400 mg), naproxen (20 to 200 mg), indomethacin (20 to 200 mg) and acetaminophen (150 to 600 mg); and anti-depressants, such as amitriptyline hydrochloride (10 to 50 mg), methylphenidate hydrochloride (5 to 20 mg), d-amphetamine (5 to 20 mg), d-amphetamine sulfate (2 to 15 mg), methamphetamine hydrochloride (2 to 15 mg), depending upon the condition being treated.

EXAMPLE 10

A sterile aqueous suspension suitable for intramuscular injection and containing in each milliliter 25 mg of 3,4-Dichloro-N-[[8-(dimethylamino)-1,4-dioxaspiro[4.5]dec-8-yl]methyl]benzamide as the essential active ingredient is prepared from the following ingredients:

| Essential active ingredient | 2.5 g |
| --- | --- |
| Polyethylene glycol 4000, U.S.P. | 3 g |
| Sodium chloride | 0.9 g |
| Polysorbate 80, U.S.P. | 0.4 g |
| Sodium metabisulfite | 0.1 g |
| Methylparaben, U.S.P. | 0.18 g |
| Propylparaben, U.S.P. | 0.02 g |
| Water for injection, q.s. to | 100 ml |

The preceding sterile injectable is useful in the treatment of pain at a dose of ½ to 2 ml.

EXAMPLE 11

One thousand tablets for oral use, each containing 40 mg of N-[[4-benzyl-1-(dimethylamino)-cyclohexyl]methyl]-3,4-dichlorobenzamide as the essential active ingredient are prepared from the following ingredients:

| Essential active ingredient | 40 g |
| --- | --- |
| Dicalcium phosphate | 150 g |
| Methylcellulose, U.S.P. (15 cps) | 6.5 g |
| Talc | 20 g |
| Calcium Stearate | 2.0 g |

The essential active ingredient and dicalcium phosphate are mixed well, granulated with 7.5% aqueous solution of methylcellulose, passed through a No. 8 screen and dried carefully. The dried granules are passed through No. 12 screen, mixed with the talc and stearate and compressed into tablets. These tablets are useful in the treatment of pain in adult humans at a dose of 1 tablet one to four times a day, as needed.

One thousand 2-piece hard gelatin capsules for oral use, each capsule containing 20 mg of 3,4-Dichloro-N-[(8-(dimethylamino)-1,4-dioxaspiro[4.5]dec-8-yl)methyl]-benzamide as the essential active ingredient are prepared from the following ingredients:

| Essential active ingredient | 20 g |
| --- | --- |
| Lactose, U.S.P. | 100 g |
| Starch, U.S.P. | 10 g |
| Talc, U.S.P. | 5 g |
| Calcium Stearate | 1 g |

The finely powdered materials are mixed thoroughly, then filled into hard gelatin capsules of appropriate size.

One capsule four times a day is useful for the treatment of pain in adult humans.

I claim:

1. A compound of the formula

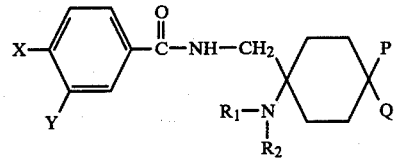

wherein each of $R_1$ and $R_2$ is $C_1$ to $C_3$-alkyl,

P, taken separately, is benzyl or methyl,

Q, taken separately, when P is benzyl or methyl, is hydrogen or hydroxy, but P is not methyl when Q is hydrogen;

P and Q, taken together, complete an alkylene dioxy group selected from the group consisting of ethylenedioxy, 1,3-propylenedioxy and 1,3-propylenedioxy having one or two methyl groups on carbon two of the propylene chain;

X is selected from the group consisting of a halogen having an atomic number of from 9 to 35, trifluoromethyl, $C_1$ to $C_3$-alkyloxy or nitro; and Y is a halogen having an atomic number of from 9 to 35 or hydrogen, and Y is hydrogen when X is trifluoromethyl or nitro, and X can also be methoxy when Y is bromine, and the hydrates and pharmacologically acceptable salts thereof.

2. A compound according to claim 1 wherein each of $R_1$ and $R_2$ is $C_1$ to $C_3$-alkyl; P and Q are taken together to complete an ethylenedioxy ring moiety, and each of X and Y is a halogen having an atomic number of from 9 to 35, and the pharmacologically acceptable salts thereof.

3. A compound according to claim 2 wherein the compound is 3,4-dichloro-N-[[8-(dimethylamino)-1,4-dioxaspiro[4.5]dec-8-yl]methyl]benzamide, or a pharmacologically acceptable salt thereof.

4. A compound according to claim 1 wherein each of $R_1$ and $R_2$ is $C_1$ to $C_3$-alkyl;
P and Q are taken together to complete a 1,3-propylenedioxy moiety, and each of X and Y is a halogen having an atomic number of from 9 to 35, and the pharmacologically acceptable salts thereof.

5. A compound according to claim 4 wherein the compound is 3,4-dichloro-N-[[9-(dimethylamino)-1,5-dioxaspiro[5.5]undec-9-yl]methyl]benzamide, or a pharmacologically acceptable salt thereof.

6. A compound according to claim 1 wherein each of $R_1$ and $R_2$ is $C_1$ to $C_3$-alkyl;
P is benzyl;
Q is hydrogen; and each of X and Y is halogen having an atomic number of from 9 to 35, and the pharmacologically acceptable salts thereof.

7. A compound according to claim 6 wherein the compound is N-[[4-benzyl-1-(dimethylamino)cyclohexyl]methyl]-3,4-dichlorobenzamide, or a pharmacologically acceptable salt thereof.

8. A compound according to claim 1 wherein each of $R_1$ and $R_2$ is $C_1$ to $C_3$-alkyl; P is methyl; Q is hydroxy, and each of X and Y is halogen having an atomic number of from 9 to 35, and the pharmacologically acceptable salts thereof.

9. A compound according to claim 8 wherein the compound is 3,4-dichloro-N-[[1-(dimethylamino)-4-hydroxy-4-methylcyclohexyl]methyl]benzamide, or a hydrate or pharmacologically acceptable salt thereof.

10. A composition useful in pharmaceutical dosage unit form for alleviating pain in warm-blooded mammals which comprises a pain-alleviating effective nontoxic amount of a compound of formula I in claim 1 in combination with a pharmaceutically acceptable carrier.

11. A composition according to claim 10 wherein the essential active ingredient for alleviating pain is a compound according to claim 2.

12. A composition according to claim 10 wherein the essential active ingredient for alleviating pain is a compound of claim 7.

13. A method for alleviating pain which comprises administering to a warm-blooded animal a pain-alleviating effective amount of a compound of formula I in claim 1 in a pharmaceutical dosage unit form.

14. A method according to claim 12 wherein the pain alleviating compound is a compound of claim 2.

15. A method according to claim 12 wherein the pain alleviating compound is a compound of claim 7.

16. A compound according to claim 1 wherein each of $R_1$ and $R_2$ is $C_1$ to $C_3$-alkyl; P and Q are taken together to complete a 2,2-dimethyl-1,3-propylenedioxy ring moiety, and each of X and Y is a halogen having an atomic number of from 9 to 35, and the pharmacologically acceptable salts thereof.

17. A compound according to claim 16 which is 3,4-dichloro-N-[[9-(dimethylamino)-3,3-dimethyl-1,5-dioxaspiro[5.5]undec-9-yl]methyl]-benzamide, or a pharmacologically acceptable salt thereof.

18. A compound according to claim 1 wherein $R_1$ and $R_2$ are each $C_1$ to $C_3$-alkyl; P and Q are taken together to complete an ethylenedioxy ring moiety; X is trifluoromethyl and Y is hydrogen; and the pharmacologically acceptable salts thereof.

19. A compound according to claim 18 wherein the compound is $\alpha,\alpha,\alpha$-trifluoro-N-[[8-(dimethylamino)-1,4-dioxaspiro[4.5]dec-8-yl]-p-toluamide], or a pharmacologically acceptable salt thereof.

20. A compound according to claim 1 wherein each of $R_1$ and $R_2$ is $C_1$ to $C_3$-alkyl; P and Q are taken together to complete an ethylenedioxy ring moiety; X is a $C_1$ to $C_3$-alkyloxy, Y is a halogen having an atomic number of from 9 to 35; or a pharmacologically acceptable salt thereof.

21. A compound according to claim 20 wherein the compound is 3-bromo-N-[[8-(dimethylamino)-1,4-dioxaspiro[4.5]dec-8-yl]methyl]-4-methoxybenzamide, or a pharmacologically acceptable salt thereof.

22. A compound according to claim 1 wherein each of $R_1$ and $R_2$ is $C_1$ to $C_3$-alkyl; P and Q are taken together to complete an ethylenedioxy ring moiety; X is nitro and Y is hydrogen, or a pharmacologically acceptable salt thereof.

23. A compound according to claim 22 wherein the compound is N-[[8-(dimethylamino)-1,4-dioxaspiro[4.5]dec-8-yl]methyl]-4-nitrobenzamide, or a pharmacologically acceptable salt thereof.

* * * * *